United States Patent
Yamka et al.

(10) Patent No.: US 9,168,240 B2
(45) Date of Patent: Oct. 27, 2015

(54) PET FOOD COMPOSITIONS AND METHODS FOR WEIGHT LOSS AND MAINTENANCE

(75) Inventors: Ryan Michael Yamka, Succasunna, NJ (US); Nolan Zebulon Frantz, Andover, NJ (US); Samer Al-Murrani, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 13/997,353

(22) PCT Filed: Nov. 30, 2011

(86) PCT No.: PCT/US2011/062526
§ 371 (c)(1),
(2), (4) Date: Jun. 24, 2013

(87) PCT Pub. No.: WO2012/087511
PCT Pub. Date: Jun. 28, 2012

(65) Prior Publication Data
US 2013/0281533 A1    Oct. 24, 2013

Related U.S. Application Data

(60) Provisional application No. 61/426,629, filed on Dec. 23, 2010.

(51) Int. Cl.
| | | |
|---|---|---|
| A61K 31/20 | (2006.01) | |
| A61K 31/015 | (2006.01) | |
| A23K 1/18 | (2006.01) | |
| A23K 1/16 | (2006.01) | |

(52) U.S. Cl.
CPC .............. *A61K 31/20* (2013.01); *A23K 1/1603* (2013.01); *A23K 1/164* (2013.01); *A23K 1/1606* (2013.01); *A23K 1/1609* (2013.01); *A23K 1/1846* (2013.01); *A23K 1/1866* (2013.01); *A61K 31/015* (2013.01)

(58) Field of Classification Search
CPC ..... A61K 31/20; A61K 31/015; A23K 1/164; A23K 1/1609; A23K 1/1606
See application file for complete search history.

(56) References Cited

U.S. PATENT DOCUMENTS

| | | | | |
|---|---|---|---|---|
| 6,133,323 | A * | 10/2000 | Hayek | 514/725 |
| 6,914,071 | B2 * | 7/2005 | Zicker et al. | 514/440 |
| 2008/0233248 | A1 | 9/2008 | Swenke et al. | |
| 2008/0312132 | A1 | 12/2008 | Miller et al. | |
| 2011/0269828 | A1 | 11/2011 | Frantz | |

FOREIGN PATENT DOCUMENTS

| | | |
|---|---|---|
| CN | 1454495 | 11/2003 |
| EP | 1602284 | 12/2005 |
| WO | WO 03/088764 | 10/2003 |
| WO | WO 2005/025322 | 3/2005 |
| WO | WO 2005/077386 | 8/2005 |
| WO | WO 2007/019549 | 2/2007 |
| WO | WO 2008/103180 | 8/2008 |
| WO | WO 2009/046964 | 4/2009 |
| WO | WO 2011/011472 | 1/2011 |
| WO | WO 2012/087486 | 6/2012 |

OTHER PUBLICATIONS

Nutritional Information for Paprika (http://nutritiondata.self.com/facts/spices-and-herbs/198/2#; Accessed Jan. 30, 2015).*
Association of American Feed Control Officials (AAFCO) Official Publication (2003, pp. 126-140).*
Hand, "Chapter 13: Obesity," Small Animal Clinical Nutrition, 4th ed., pp. 401-430, 2000.
International Search Report and Written Opinion in International Application No. PCT/US11/062526, mailed Feb. 17, 2012.
Jewell et al., 2000, "Effect of increasing dietary antioxidants on concentrations of vitamin E and total alkenals in serum of dogs and cats," Vet. Ther. 1(4):264-272.
Nelson et al., 2000, "Effect of dietary insoluble fiber on control of glycemia in cats with naturally acquired diabetes mellitus," J. Amer. Vet. Med. Assoc. 216:1082-1088.
Wong-Valle et al., 1989, "Bioavailability of manganese from feed grade manganese oxides for broiler chicks," Poultry Science 68(10):1368-1373.
Written Opinion in International Application No. PCT/US11/062526, mailed Dec. 14, 2012.
Yamka et al., 2006, "In vivo measurement of flatulence and nutrient digestibility in dogs fed poultry by-product meal, conventional soybean meal, and low-oligosaccharide low-phytate soybean meal," Amer. J. Vet. Res. 67(1):88-94.
Yamka et al., 2006, "Measurement of arthritic and bone serum metabolites in arthritic, non-arthritic, and geriatric dogs fed wellness foods," Int. J. Appl. Res. Vet. Med. 4:255-264.
Yu et al., 2006, "Dietary supplements of Vitamins E and C and β-carotene reduce oxidative stress in cats with renal insufficiency," Vet. Res. Commun. 30(4):403-413.
May, 1994, "Palm Oil Carotenoids," Food and Nutrition Bulletin 15(2):online    http://archive.unu/edu/unupress/food/8F152e/8F152E05.htm.
Ding Xiaowen et al., 2008, "The Principle of Health Food," Principles of Dietary Supplement, 1st ed., p. 178.
Ling Guanting, 2007, "Healthy Food Material Manual," Dietary Supplement Raw Material Handbook, 2nd ed., p. 540.
Lu Qi-Yu, 2004, Oil Chemical Products Production Technology, p. 4.
Plumb, 2009, "Carnitine Levocarnitine L-Carnitine," Plumb's Veterinary Drug Handbook, 1st ed., p. 166.
Tong et al., 2009, "Chapter Four: Special Subjects," Biochemistry, 2nd ed., p. 404.

(Continued)

*Primary Examiner* — James D Anderson

(57) ABSTRACT

The present invention provides food compositions and methods for companion animals that are effective in preventing or treating obesity.

16 Claims, No Drawings

(56) References Cited

OTHER PUBLICATIONS

Xie, 2004, "Who Touched My Menu," The New Concept of Health Series, http://www.shulikxhhx.cn/n/print.jsp p. 35.

Zhu Hongfa, 2003, "41. Tetradecanoic Acid," Handbook of Common Materials for Fine Chemical Industry, 1st ed., p. 51.

\* cited by examiner

PET FOOD COMPOSITIONS AND METHODS FOR WEIGHT LOSS AND MAINTENANCE

This present application is a national stage entry under 35 U.S.C. §371 of International Patent Application No. PCT/US2011/062526, filed Nov. 30, 2011, which claims benefit of U.S. Provisional Patent Application No. 61/426,629 filed Dec. 23, 2010, the contents of which are hereby incorporated by reference in their entireties.

FIELD OF THE INVENTION

The present invention relates to pet food compositions and methods for preventing or treating obesity in companion animals, particularly canines and felines.

BACKGROUND OF THE INVENTION

Generally, companion animals such as canines and felines weighing more than 15% of their ideal body weight are considered overweight or obese. Overweight animals generally have an excess of body adipose tissue. The most common cause of an animal being overweight is an over consumption of food that results in an excess intake of calories. However, there are other factors that can increase an animal's chances for being overweight, e.g., lifestyle, health, eating habits, breed, spaying, and neutering. Also, the incidence of animals becoming overweight generally increases with age due to a general decrease in metabolic rate and in physical activity. Surveys estimate that 25% of canines in the United States that visit veterinary clinics are fat to the point of being obese. Studies have shown that fat animals are significantly more at risk for diseases such as arthritis, heart disease, respiratory disease, diabetes, bladder cancer, hypothyroidism, and pancreatitis.

Losing weight or maintaining weight, particularly for a companion animal, is difficult. It is necessary to modulate the caloric intake of the animal. Modulating the amount of adipose tissue on a companion animal, including preventing an animal from becoming overweight or treating a fat animal to reduce the amount of adipose tissue on the animal, is also difficult. An effective way to prevent an animal from becoming fat or to reduce the amount of fat on an animal is with dietary restriction and exercise. However, it is often difficult to ensure compliance with diet and exercise programs.

Given the problems with current methods for dealing with the prevention or treatment of obesity in companion animals such as canines and felines, there is a continuing need for new methods and compositions useful for treating and preventing weight conditions such as obesity and, in particular, for food compositions effective in preventing and treating these conditions.

BRIEF SUMMARY OF THE INVENTION

The invention advantageously provides an effective functional food-based approach to the reduction and control of weight in companion animals such as canines and felines. The invention is characterized by the use of a combination of myristic acid and beta-carotene in a nutritionally complete pet food composition, such as a nutritionally complete canine or feline food composition. A food composition of the invention may, for example, include a combination of tomato pomace, coconut oil and carrot powder.

One embodiment of the invention provides a pet food composition that includes a myristic acid source and a beta-carotene source, in amounts effective to prevent or treat obesity in a companion animal. The myristic acid source may, for example, include or consist of coconut oil, and the beta-carotene source may include or consist of at least one of tomato pomace and carrot powder.

A related embodiment of the invention provides a method for preventing or treating obesity in a companion animal such as a canine or a feline, which includes feeding to a companion animal in need of prevention or treatment of obesity a composition of the invention. The composition may, for example, be fed to the animal as its primary or sole nutritionally complete food on a daily basis.

A further embodiment provides the use of a myristic acid source and a beta-carotene source for the manufacture of a weight-loss and maintenance pet food composition for a companion animal, such as a canine or a feline.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

As used herein, the terms "overweight", "fat", "obese", "obesity" and like terms refer to a body weight condition of an animal that is more than its' ideal weight. For example, the term "fat" as applied to an animal can mean any animal that is determined to have an excess amount of body adipose tissue or an animal that is prone to developing an excess amount of body adipose tissue using techniques and methods known to veterinary care professionals and others of skill in the art. For example, an animal is considered "fat" if (1) the animal has a Body Mass Index (BMI) of 25 or more (a number considered to include "overweight" and "obese" animals in some methods of characterizing animal conditions), (2) the animal's weight is 15% or more than its "ideal" body weight as defined by veterinary care professionals, or as known to one of skill in the art, (3) an animal's percent body fat is 27% or more as determined by dual-energy X-ray absorptiometry ("DEXA"), or (4) an animal has a body condition score ("BCS") of more than 3 on a scale from 1 to 5 as determined by one of skill in the art using the method disclosed in "Small Animal Clinical Nutrition", 4$^{th}$ Edition, in Chapter 13 (ISBN 0-945837-05-4) or its equivalent using other BCS methods.

As used herein, "treatment of obesity" refers to the reduction of body weight of an obese animal until the animal has achieved its ideal body weight, as determined according to conventional methods, e.g., by administering an effective amount of a composition of the present invention to an animal. "Prevention of obesity" refers to preventing an animal from attaining a body weight condition that would be deemed by one of skill in the art as being more than ideal for the animal, by administering an effective amount of a composition of the present invention to the animal.

As used herein, "an amount effective", "an effective amount", and like terms refer to that amount of a compound, material or composition as described herein that may be effective to achieve a particular biological result. Such results may include, but are not limited to, the treatment and/or prevention of obesity. Such effective activity may be achieved, for example, by administration of compositions of the present invention to an animal. An effective amount may be based on several factors, including an animal's ideal weight, the metabolizable energy of the composition, and frequency of feeding the animal compositions of the present invention, e.g., once, twice, or three times daily, and other compositions fed to the animal.

As used herein, the term primary food composition means the main, nutritionally comprehensive meal food that the canine or feline is fed day to day.

As contemplated herein, the compositions of the present invention are meant to encompass nutritionally complete and balanced animal food compositions. A "nutritionally complete diet" is a diet that includes sufficient nutrients for maintenance of normal health of a healthy animal on the diet. Nutritionally complete and balanced pet food compositions are familiar to one of skill in the art.

For example, a nutritionally complete and balanced dog food composition of the present invention may comprise: about 0 to about 90%, preferably about 5% to 60%, by weight of carbohydrates; about 5% to about 70%, preferably about 10% to about 60%, more preferably about 20% to about 50%, by weight of protein: about 1% to about 50%, preferably about 2% to about 40%, more preferably about 3% to about 15%, by weight of fat; about 0.1% to about 40%, preferably about 1% to about 30%, more preferably about 15% to about 50%, by weight of total dietary fiber; about 0 to about 15%, preferably about 2% to about 8%, by weight of vitamins and minerals, antioxidants, and other nutrients which support the nutritional needs of the animal.

Protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. The amount of "crude protein" in a composition disclosed herein may be determined based on the amount of nitrogen in the composition according to methods familiar to one of skill in the art. As contemplated herein, the compositions of the present invention may comprise from about 5% to about 70% protein, from about 10% to about 60% protein, from about 20% to about 50% protein, from about 25% to about 40% protein, and from about 29% to about 38% protein.

In certain embodiments, the nutritionally complete pet food compositions disclosed herein may comprise fat. Sources of fat for the compositions of the present invention can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. As contemplated herein, the compositions of the present invention may comprise from about 1% to about 20% fat, from about 2% to about 18% fat, from about 3% to about 15% fat, from about 7% to about 14% fat, and from about 9% to about 12% fat.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NFE"), which may be calculated as follows: NFE=100%−moisture %−protein %−fat %−ash %−crude fiber %.

Total dietary fiber refers to components of a plant which are resistant to digestion by an animal's digestive enzymes. Total dietary fiber includes soluble and insoluble fibers. As contemplated herein, the compositions of the present invention may comprise from about 15% to about 50% total dietary fiber, from about 16% to about 45% total dietary fiber, from about 17% to about 40% total dietary fiber, from about 18% to about 35% total dietary fiber, from about 19% to about 30% total dietary fiber, and from about 20% to about 29% total dietary fiber.

Soluble fiber is resistant to digestion and absorption in the small intestine and undergoes complete or partial fermentation in the large intestine. Sources of soluble fiber may include beet pulp, guar gum, chicory root, psyllium, pectin, blueberry, cranberry, squash, apples, oats, beans, citrus, barley, or peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber.

Crude fiber includes indigestible components contained in cell walls and cell contents of plants such as grains, e.g., hulls of grains such as rice, corn, and beans.

The invention is further described in the following examples. The examples are merely illustrative and do not in any way limit the scope of the invention as described and claimed.

EXAMPLES

Example 1

General Materials and Method

The animal compositions were prepared as follows: each food was kibbled and formulated in accordance with the Association of American Feed Control Officials nutrient guide for cats or dogs and balanced to meet adult maintenance requirements. The animals were cared for in accordance with Institutional Animal Care and Use Committee protocols.

TABLE 1

| Ingredients in Canine and Feline Weight Formulas ||
| Canine Weight Formula | Feline Weight Formula |
| --- | --- |
| Poultry by-product meal | Poultry by-product meal |
| Corn gluten meal | Corn gluten meal |
| Cellulose | Cellulose |
| Soybean meal | Soybean meal |
| Beet pulp | Beet pulp |
| Whole Flaxseed | Whole Flaxseed |
| Soybean oil | Soybean oil |
| Carrot powder | Carrot powder |

TABLE 1-continued

Ingredients in Canine and Feline Weight Formulas

| Canine Weight Formula | Feline Weight Formula |
|---|---|
| L-lysine | L-lysine |
| DL-methionine | DL-methionine |
| Potassium chloride | Potassium chloride |
| L-carnitine | L-carnitine |
| Coconut oil | Coconut oil |
| Vitamin E oil | Vitamin E oil |
| Choline chloride | Choline chloride |
| Taurine | Taurine |
| Tomato Pomace | Tomato Pomace |
| Pal enhancer | Pal enhancer |
| Vitamin premix | Vitamin premix |
| Mineral premix | Mineral premix |
| Pea bran meal | Rice |
| Soybean mill run | Citrus pulp |
| Dicalcium phosphate | Calcium sulfate |
| Lipoic acid* | Lipoic Acid* |
| Corn | |
| Salt | |

*Lipoic Acid not included in Formulas FA and CB.

Blood or serum samples were stored at −80° C. until analysis. Samples were extracted and prepared for analysis using standard solvent extraction methods. The extracted samples were split into equal parts for analysis on the GC/MS and LC/MS/MS platforms in a randomized run order. Data for each compound were normalized by calculating the median values for each run-day ("block normalization").

Data were analyzed either using SAS version 9.0 or a t-test to determine treatment differences. Paired t-test was used to determine if there were significant changes from baseline (month 0). The experimental unit was canine (dog) or feline (cat) and differences were considered significant when $P<0.05$.

Example 2

Formulation of Compositions

The following compositions in Table 2 are formulated in accordance with the Association of American Feed Control Officials nutrient guide for dogs and cats, balanced to meet adult maintenance requirements, and extruded as a dry kibble. The contents of the compositions are analyzed by methods known in the art such as Kjeldhal analysis for protein.

TABLE 2

Nutrient composition of the foods used in the study (as analyzed)

| Nutrient, 100% Dry Matter Basis | Units | Formula FA | Formula FB | Formula CA | Formula CB |
|---|---|---|---|---|---|
| Protein | % | 37.95 | 38.51 | 29.6 | 29.3 |
| Arginine | % | 2.22 | 2.29 | 1.56 | 1.60 |
| Cystine | % | 0.59 | 0.60 | 0.50 | 0.49 |
| Histidine | % | 0.80 | 0.81 | 0.58 | 0.59 |
| Isoleucine | % | 1.59 | 1.62 | 1.09 | 1.11 |
| Leucine | % | 4.37 | 4.38 | 2.78 | 2.81 |
| Lysine, | % | 2.12 | 2.11 | 1.59 | 1.60 |
| Methionine | % | 1.39 | 1.41 | 1.29 | 1.25 |
| Phenylalanine | % | 2.02 | 2.04 | 1.34 | 1.34 |
| Threonine | % | 1.44 | 1.48 | 1.02 | 1.03 |
| Tryptophan | % | 0.32 | 0.33 | 0.26 | 0.26 |
| Tyrosine | % | 1.35 | 1.44 | 0.90 | 0.92 |
| Valine | % | 1.93 | 1.97 | 1.33 | 1.34 |
| Lysine:calorie ratio (calculated) | | | 11.62 | 4.76 | 4.78 |
| Fat, crude by acid Hydrolysis | % | 11.39 | 11.62 | 11.67 | 11.78 |
| C12:0 Dodecanoic (Lauric) | % | 0.86 | 0.85 | 1.17 | 1.23 |
| C14:0 Tetradecanoic (Myristic) | % | 0.36 | 0.36 | 0.49 | 0.51 |
| C18:2 Octadecadienoic (Linoleic) | % | 2.67 | 2.77 | 3.04 | 3.09 |
| C18:3 Octadecatrienoic (Linolenic) | % | 1.16 | 1.15 | 0.76 | 0.75 |
| Total Dietary Fiber | % | 20.05 | 21.24 | 29.4 | 28.2 |
| Insoluble Fiber | % | 17.43 | 20.26 | 26.4 | 25.4 |
| Soluble Fiber | % | 2.62 | 0.98 | 3.0 | 2.8 |
| % Crude Fiber | % | 10.46 | 9.48 | 15.0 | 14.4 |
| Ash | % | 6.20 | 6.69 | 5.88 | 5.71 |
| Calcium | % | 0.96 | 0.98 | 0.88 | 0.88 |
| Chloride-Soluble | % | 0.73 | 0.71 | 0.88 | 0.87 |
| Magnesium | % | 0.11 | 0.11 | 0.17 | 0.17 |
| Phosphorus | % | 0.81 | 0.83 | 0.69 | 0.70 |
| Potassium | % | 0.80 | 0.78 | 0.78 | 0.78 |
| Sodium | % | 0.27 | 0.27 | 0.36 | 0.36 |
| Carnitine, L (same as Free) | mg/kg | 639 | 633 | 268 | 282 |
| Beta Carotene | Ppm | 3.56 | 3.31 | | |
| Total Lycopene | uG/G | | | 3.59 | 3.44 |
| Manganese | ppm | | | 108 | 105 |
| Lipoic acid | ppm | — | 39 | 105.43 | — |

Example 3

Feline (Cat) Weight Loss and Maintenance Study

Forty cats were employed in a four month weight loss study and divided into two treatment groups, twenty cats for each, and fed with either Formula FA or Formula FB. All cats began the study with greater than 31.6% body fat of total weight. The cats remained on the weight loss study for a period of four months or until optimal body weight, i.e., 20% body fat, was achieved.

Cats were removed from the study when they reached the optimal weight or were diagnosed with a health condition such as renal disease, hyperthyroidism, or others. In addition, cats that refused to eat at least 25% of their assigned food for more than four days or had weight loss exceeding 2.0% weekly were removed from the study. If any necessary treatment involved switching a cat to another food for more than four days, the cat was removed from the study.

When a cat was removed with a positive end point (achieved ideal body weight), the animal was continued to be included in the analysis using LOCF (last observation carry forward) method to handle missing data for all measured variables except intake.

Body weight was monitored weekly to avoid excess weight loss; food intake was monitored daily. Dual-energy x-ray absorptiometry (DXA) scans were performed at month 0, 1, 2, 3, and 4 to assess the effect of treatment by monitoring parameters such as body weight, total fat mass, % body fat and lean. Blood samples were collected at month 0, 1, 2, 3, and 4 to analyze for chemistry screens to monitor the health of all animals on the study. Blood samples at month 0, 1, 2, 3 and 4 were also analyzed for metabolomics.

Results of the study are provided in the following tables.

TABLE 3

Weight Loss Study: Total Body Weight Loss by DXA (g)

| Parameter Measured | Formula FA | | Formula FB | | Formula FA vs Formula FB* |
|---|---|---|---|---|---|
| | N | Mean ± SEM | N | Mean ± SEM | |
| Observed Month 0 | 20 | 6603.25 ± 353 | 20 | 6026.07 ± 461 | NS |
| Observed Month 1 | 19 | 5970.26 ± 315 | 20 | 5709.80 ± 380 | NS |
| Observed Month 2 | 20 | 5636.70 ± 302 | 20 | 5453.30 ± 309 | NS |
| Observed Month 3 | 20 | 5193.75 ± 283 | 20 | 5028.20 ± 276 | NS |
| Observed Month 4 | 20 | 5044.60 ± 274 | 20 | 4888.90 ± 268 | NS |
| Change from Month 0 to 1 | 19 | −521.74 ± 60.4 | 20 | −316.27 ± 124 | NS |
| Change from Month 0 to 2 | 20 | −966.55 ± 64.6 | 20 | −572.77 ± 300 | NS |
| Change from Month 0 to 3 | 20 | −1409.5 ± 87.6 | 20 | −997.87 ± 338 | NS |
| Change from Month 0 to 4 | 20 | −1558.7 ± 106 | 20 | −1137.2 ± 343 | NS |
| Month 0 vs 1** | | <0.01 | | 0.02 | |
| Month 0 vs 2** | | <0.01 | | 0.07 | |
| Month 0 vs 3** | | <0.01 | | <0.01 | |
| Month 0 vs 4** | | <0.01 | | <0.01 | |

NS = Not significant (i.e., p-values > 0.1)
*t-Test,
**paired t-test

TABLE 4

Weight Loss Study: Total Body Fat by DXA (g)

| Parameter Measured | Formula FA | | Formula FB | | Formula FA vs Formula FB* |
|---|---|---|---|---|---|
| | N | Mean ± SEM | N | Mean ± SEM | |
| Observed Month 0 | 20 | 2708.05 ± 234 | 20 | 2365.27 ± 227 | NS |
| Observed Month 1 | 19 | 2356.11 ± 200 | 20 | 2236.45 ± 166 | NS |
| Observed Month 2 | 20 | 1906.90 ± 177 | 20 | 1894.00 ± 231 | NS |
| Observed Month 3 | 20 | 1523.20 ± 164 | 20 | 1412.50 ± 140 | NS |
| Observed Month 4 | 20 | 1359.70 ± 143 | 20 | 1282.60 ± 133 | NS |
| Change from Month 0 to 1 | 19 | −298.89 ± 62.6 | 20 | −128.82 ± 126 | NS |
| Change from Month 0 to 2 | 20 | −801.15 ± 70.2 | 20 | −471.27 ± 295 | NS |
| Change from Month 0 to 3 | 20 | −1184.9 ± 80.7 | 20 | −952.77 ± 179 | NS |
| Change from Month 0 to 4 | 20 | −1348.4 ± 105 | 20 | −1082.7 ± 185 | NS |
| Month 0 vs 1** | | <0.01 | | NS | |
| Month 0 vs 2** | | <0.01 | | NS | |
| Month 0 vs 3** | | <0.01 | | <0.01 | |
| Month 0 vs 4** | | <0.01 | | <0.01 | |

NS = Not significant (i.e., p-values > 0.1)
*t-Test,
**paired t-test

TABLE 5

Weight Loss Study: Percent Body Fat Loss by DXA (%)

| Parameter Measured | Formula FA | | Formula FB | | Formula FA vs Formula FB* |
|---|---|---|---|---|---|
| | N | Mean ± SEM | N | Mean ± SEM | |
| Observed Month 0 | 20 | 40.06 ± 1.54 | 20 | 39.13 ± 1.26 | NS |
| Observed Month 1 | 19 | 38.72 ± 1.54 | 20 | 38.19 ± 1.27 | NS |
| Observed Month 2 | 20 | 32.98 ± 1.62 | 20 | 31.28 ± 1.58 | NS |
| Observed Month 3 | 20 | 28.21 ± 1.69 | 20 | 27.06 ± 1.54 | NS |
| Observed Month 4 | 20 | 26.10 ± 1.48 | 20 | 25.23 ± 1.48 | NS |
| Change from Month 0 to 1 | 19 | −1.21 ± 0.65 | 20 | −0.93 ± 0.88 | NS |
| Change from Month 0 to 2 | 20 | −7.08 ± 0.6 | 20 | −7.84 ± 0.88 | NS |
| Change from Month 0 to 3 | 20 | −11.85 ± 0.62 | 20 | −12.07 ± 0.96 | NS |
| Change from Month 0 to 4 | 20 | −13.96 ± 0.72 | 20 | −13.89 ± 1.17 | NS |
| Month 0 vs 1** | | 0.08 | | NS | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values > 0.1)
*t-Test,
**paired t-test

TABLE 6

Weight Loss Study: Lean Mass by DXA (g)

| Parameter Measured | Formula FA N | Formula FA Mean ± SEM | Formula FB N | Formula FB Mean ± SEM | Formula FA vs Formula FB* |
|---|---|---|---|---|---|
| Observed Month 0 | 20 | 3745.80 ± 158 | 20 | 3684.15 ± 158 | NS |
| Observed Month 1 | 19 | 3472.16 ± 152 | 20 | 3482.95 ± 176 | NS |
| Observed Month 2 | 20 | 3581.30 ± 162 | 20 | 3573.60 ± 164 | NS |
| Observed Month 3 | 20 | 3526.30 ± 151 | 20 | 3472.55 ± 152 | NS |
| Observed Month 4 | 20 | 3541.35 ± 160 | 20 | 3464.25 ± 150 | NS |
| Change from Month 0 to 1 | 19 | −219.47 ± 29.5 | 20 | −201.20 ± 50.6 | NS |
| Change from Month 0 to 2 | 20 | −164.50 ± 26 | 20 | −110.55 ± 49.8 | NS |
| Change from Month 0 to 3 | 20 | −219.50 ± 23.9 | 20 | −211.60 ± 42.5 | NS |
| Change from Month 0 to 4 | 20 | −204.45 ± 29.5 | 20 | −219.90 ± 43.8 | NS |
| Month 0 vs 1** | | <0.01 | | <0.01 | |
| Month 0 vs 2** | | <0.01 | | 0.04 | |
| Month 0 vs 3** | | <0.01 | | <0.01 | |
| Month 0 vs 4** | | <0.01 | | <0.01 | |

NS = Not significant (i.e., p-values > 0.1)
*t-Test,
**paired t-test

The results indicate that although the test animals lost lean muscle in the first one month of the study, the level of lean muscle was maintained during the study while the animals statistically lost about 15% body weight or about 42-53% of body fat to achieve about 25±3% of mean body fat.

The weight loss of the animals also resulted in a reduction of IGF-1 and leptin, which was maintained after weight loss. The results are shown below.

TABLE 7

Weight Loss Study: IGF-1 (ng/ml)

| Parameter Measured | Formula FA N | Formula FA Mean ± SEM | Formula FB N | Formula FB Mean ± SEM | Formula FA vs Formula FB* |
|---|---|---|---|---|---|
| Observed Month 0 | 19 | 4.95 ± 0.31 | 20 | 4.80 ± 0.28 | NS |
| Observed Month 1 | 19 | 4.13 ± 0.29 | 19 | 4.29 ± 0.31 | NS |
| Observed Month 2 | 20 | 4.23 ± 0.25 | 20 | 4.36 ± 0.36 | NS |
| Observed Month 3 | 20 | 4.00 ± 0.32 | 20 | 4.05 ± 0.35 | NS |
| Observed Month 4 | 20 | 3.92 ± 0.34 | 20 | 4.20 ± 0.35 | NS |
| Change from Month 0 to 1 | 18 | −0.81 ± 0.19 | 19 | −0.56 ± 0.13 | NS |
| Change from Month 0 to 2 | 19 | −0.61 ± 0.19 | 20 | −0.43 ± 0.2 | NS |
| Change from Month 0 to 3 | 19 | −0.90 ± 0.16 | 20 | −0.75 ± 0.18 | NS |
| Change from Month 0 to 4 | 19 | −0.99 ± 0.23 | 20 | −0.59 ± 0.21 | NS |
| Month 0 vs 1** | | <0.01 | | <0.01 | |
| Month 0 vs 2** | | <0.01 | | 0.04 | |
| Month 0 vs 3** | | <0.01 | | <0.01 | |
| Month 0 vs 4** | | <0.01 | | 0.01 | |

NS = Not significant (i.e., p-values > 0.1
*t-Test,
**paired t-test

TABLE 8

Weight Loss Study: Leptin (ng/ml)

| Parameter Measured | Formula FA N | Formula FA Mean ± SEM | Formula FB N | Formula FB Mean ± SEM | Formula FE vs Formula FB* |
|---|---|---|---|---|---|
| Observed Month 0 | 19 | 2.93 ± 0.36 | 20 | 3.91 ± 0.85 | NS |
| Observed Month 1 | 19 | 2.61 ± 0.48 | 19 | 2.24 ± 0.32 | NS |
| Observed Month 2 | 20 | 1.98 ± 0.31 | 20 | 2.80 ± 0.59 | NS |
| Observed Month 3 | 20 | 1.94 ± 0.42 | 20 | 1.99 ± 0.57 | NS |
| Observed Month 4 | 20 | 1.56 ± 0.42 | 20 | 1.70 ± 0.34 | NS |
| Change from Month 0 to 1 | 18 | −0.33 ± 0.36 | 19 | −0.95 ± 0.25 | NS |
| Change from Month 0 to 2 | 19 | −0.88 ± 0.24 | 20 | −1.11 ± 0.31 | NS |
| Change from Month 0 to 3 | 19 | −0.91 ± 0.42 | 20 | −1.92 ± 0.36 | 0.07 |
| Change from Month 0 to 4 | 19 | −1.32 ± 0.47 | 20 | −2.21 ± 0.54 | NS |

TABLE 8-continued

Weight Loss Study: Leptin (ng/ml)

| Parameter Measured | Formula FA | | Formula FB | | Formula FE vs |
|---|---|---|---|---|---|
| | N | Mean ± SEM | N | Mean ± SEM | Formula FB* |
| Month 0 vs 1** | | NS | | <0.01 | |
| Month 0 vs 2** | | <0.01 | | <0.01 | |
| Month 0 vs 3** | | 0.04 | | <0.01 | |
| Month 0 vs 4** | | 0.01 | | <0.01 | |

NS = Not significant (i.e., p-values > 0.1)
*t-Test,
**paired t-test

In addition, it is noted that the animals maintained their reduced weight for an additional four months.

Results are provided below.

TABLE 9

Weight Maintenance Study: Total Body Weight Loss by DXA (g)

| Parameter Measured | Formula FA | | Formula FB | | Formula FA vs |
|---|---|---|---|---|---|
| | N | Mean ± SEM | N | Mean ± SEM | Formula FB* |
| Observed Month 0 | 19 | 5005.47 ± 286 | 19 | 4985.79 ± 263 | NS |
| Observed Month 1 | 19 | 4809.37 ± 269 | 19 | 4754.11 ± 239 | NS |
| Observed Month 2 | 19 | 4711.21 ± 267 | 19 | 4600.16 ± 231 | NS |
| Observed Month 3 | 19 | 4795.00 ± 266 | 19 | 4762.47 ± 242 | NS |
| Observed Month 4 | 19 | 4882.37 ± 247 | 19 | 4823.05 ± 234 | NS |
| Change from Month 0 to 1 | 19 | 196.11 ± 41.9 | 19 | −231.68 ± 41.6 | NS |
| Change from Month 0 to 2 | 19 | −394.35 ± 42.2 | 19 | −385.63 ± 53.7 | NS |
| Change from Month 0 to 3 | 19 | −210.47 ± 43.8 | 19 | −223.32 ± 67.2 | NS |
| Change from Month 0 to 4 | 19 | −123.11 ± 56.9 | 19 | −162.74 ± 67.9 | NS |
| Month 0 vs 1** | | <0.01 | | 0.02 | |
| Month 0 vs 2** | | <0.01 | | 0.07 | |
| Month 0 vs 3** | | <0.01 | | <0.01 | |
| Month 0 vs 4** | | 0.04 | | 0.03 | |

NS = Not significant (i.e., p-values > 0.1)
*t-Test,
**paired t-test

TABLE 10

Weight Maintenance Study: Total Body Fat by DXA (g)

| Parameter Measured | Formula FA | | Formula FB | | Formula FA |
|---|---|---|---|---|---|
| | N | Mean ± SEM | N | Mean ± SEM | vs Formula FB* |
| Observed Month 0 | 19 | 1316.26 ± 144 | 19 | 1324.89 ± 133 | NS |
| Observed Month 1 | 19 | 1167.21 ± 148 | 19 | 1082.37 ± 115 | NS |
| Observed Month 2 | 19 | 1011.21 ± 155 | 19 | 889.42 ± 93.8 | NS |
| Observed Month 3 | 19 | 904.11 ± 137 | 19 | 884.68 ± 103 | NS |
| Observed Month 4 | 19 | 1040.79 ± 130 | 19 | 966.84 ± 120 | NS |
| Change from Month 0 to 1 | 19 | −149.05 ± 36.5 | 19 | −242.53 ± 39.6 | NS |
| Change from Month 0 to 2 | 19 | −305.05 ± 40.6 | 19 | −435.47 ± 56.5 | NS |
| Change from Month 0 to 3 | 19 | −412.16 ± 31 | 19 | −440.21 ± 52.4 | NS |
| Change from Month 0 to 4 | 19 | −275.47 ± 52.1 | 19 | −358.05 ± 50 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values >0.1)
*t-Test,
**paired t-test

TABLE 11

Weight Maintenance Study: Percent Body Fat Loss by DXA (%)

| Parameter Measured | Formula FA N | Formula FA Mean ± SEM | Formula FB N | Formula FB Mean ± SEM | Formula FA vs Formula FB* |
|---|---|---|---|---|---|
| Observed Month 0 | 19 | 25.48 ± 1.42 | 19 | 25.74 ± 1.46 | NS |
| Observed Month 1 | 19 | 23.23 ± 1.79 | 19 | 22.00 ± 1.58 | NS |
| Observed Month 2 | 19 | 20.30 ± 1.87 | 19 | 18.69 ± 1.25 | NS |
| Observed Month 3 | 19 | 17.84 ± 1.62 | 19 | 17.77 ± 1.43 | NS |
| Observed Month 4 | 19 | 20.65 ± 1.71 | 19 | 19.22 ± 1.84 | NS |
| Change from Month 0 to 1 | 19 | −2.26 ± 0.68 | 19 | −3.74 ± 0.63 | NS |
| Change from Month 0 to 2 | 19 | −5.18 ± 0.72 | 19 | −7.04 ± 0.68 | NS |
| Change from Month 0 to 3 | 19 | −7.64 ± 0.53 | 19 | −7.97 ± 0.67 | NS |
| Change from Month 0 to 4 | 19 | −4.84 ± 0.81 | 19 | −6.52 ± 0.77 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values >0.1)
*t-Test,
**paired t-test

TABLE 12

Weight Maintenance Study: Lean Mass by DXA (g)

| Parameter Measured | Formula FA N | Formula FA Mean ± SEM | Formula FB N | Formula FB Mean ± SEM | Formula FA vs Formula FB* |
|---|---|---|---|---|---|
| Observed Month 0 | 19 | 3546.37 ± 168 | 19 | 3516.95 ± 148 | NS |
| Observed Month 1 | 19 | 3499.95 ± 159 | 19 | 3528.84 ± 149 | NS |
| Observed Month 2 | 19 | 3558.95 ± 162 | 19 | 3568.32 ± 150 | NS |
| Observed Month 3 | 19 | 3749.00 ± 169 | 19 | 3734.84 ± 154 | NS |
| Observed Month 4 | 19 | 3698.47 ± 166 | 19 | 3711.26 ± 150 | NS |
| Change from Month 0 to 1 | 19 | −46.42 ± 33.8 | 19 | 11.89 ± 32.9 | NS |
| Change from Month 0 to 2 | 19 | 12.58 ± 32.3 | 19 | 51.37 ± 28.2 | NS |
| Change from Month 0 to 3 | 19 | 202.63 ± 37.6 | 19 | 217.89 ± 53.6 | NS |
| Change from Month 0 to 4 | 19 | 152.11 ± 42.1 | 19 | 194.32 ± 50.4 | NS |
| Month 0 vs 1** | | NS | | NS | |
| Month 0 vs 2** | | NS | | 0.08 | |
| Month 0 vs 3** | | <0.01 | | <0.01 | |
| Month 0 vs 4** | | <0.01 | | <0.01 | |

NS = Not significant (i.e., p-values >0.1)
*t-Test,
**paired t-test

TABLE 13

Weight Maintenance Study: Food Intake

| Parameter Measured | Formula FA and FB N | Mean |
|---|---|---|
| Observed Month 1 | 20 | 56 |
| Observed Month 2 | 20 | 63 |
| Observed Month 3 | 20 | 86 |
| Observed Month 4 | 20 | 101 |
| Change from Month 1 to 2 | 20 | 7 |
| Change from Month 1 to 3 | 20 | 30 |
| Change from Month 1 to 4 | 20 | 45 |

Results of the weight maintenance study showed that in the four months of weight maintenance, cats maintained their weight while increasing their food intake by 80% (45 grams vs 56 grams) consuming Formula FA or FB. Both Formula FA and FB were efficacious in reducing body weight, body fat, alkaline phosphatase, cholesterol and triglyceride levels while maintaining lean muscle. In addition, there were observed changes in biomarkers associated with lipid metabolism and obesity. Cats fed with either Formula FA or FB had a significant reduction in serum leptin levels after 4 months as well as a trend for decreases in IGF-1 levels. Both Formula FA and FB had a clinically proven reduction in serum leptin and IGF-1 levels at 2, 3, and 4 months of weight loss.

The data indicated that IGF-1 was reduced (P<0.01) at the end of the weight loss. In addition, at the end of the weight loss, cats had a reduction in leptin levels (P=0.01).

Example 4

Canine (Dog) Weight Loss and Maintenance Study

Forty dogs were employed in a four month weight loss study and divided into two treatment groups, twenty dogs for each, and fed with either Formula CA or Formula CB. All dogs began the study with greater than 33.1% body fat of total weight. The dogs remained on the weight loss study for a period of four months or until optimal body weight. i.e., 20% body fat, was achieved.

Dogs were removed from the study when they reached the optimal weight or were diagnosed with a health condition such as renal disease, hypothyroidism, or other disease. In addition, dogs that refused to eat at least 25% of their assigned food for more than four days or had weight loss exceeding 2.0% weekly were removed from the study. If any necessary treatment involved switching a dog to another food for more than four days, the dog was removed from the study.

When a dog was removed with a positive end point (achieved ideal body weight), the animal was continued to be included in the analysis using LOCF (last observation carry forward) method to handle missing data for all measured variables except intake.

Body weight was monitored weekly to avoid excess weight loss; food intake was monitored daily. Dual-energy x-ray absorptiometry (DXA) scans were performed at month 0, 1, 2, 3, and 4 to assess the effect of treatment by monitoring parameters such as body weight, total fat mass, % body fat and lean. Blood samples were collected at month 0, 1, 2, 3, and 4 to analyze for chemistry screens to monitor the health of all animals on the study. Blood samples at month 0, 1, 2, 3 and 4 were also analyzed for metabolomics.

Results of the study are provided in the following tables.

TABLE 14

Weight Loss Study: Total Body Weight Loss by DXA (g)

| | Formula CA | | Formula CB | | Formula CA |
| --- | --- | --- | --- | --- | --- |
| Parameter Measured | N | Mean ± SEM | N | Mean ± SEM | vs Formula CB* |
| Observed Month 0 | 20 | 17634.4 ± 711 | 20 | 17645.9 ± 774 | NS |
| Observed Month 1 | 20 | 16360.2 ± 669 | 20 | 16492.2 ± 797 | NS |
| Observed Month 2 | 20 | 15475.6 ± 607 | 20 | 15436.7 ± 723 | NS |
| Observed Month 3 | 20 | 14535.0 ± 551 | 20 | 15017.1 ± 654 | NS |
| Observed Month 4 | 20 | 13619.9 ± 520 | 20 | 14227.2 ± 604 | NS |
| Change from Month 0 to 1 | 20 | −1274.3 ± 86.2 | 20 | −1153.7 ± 79.5 | NS |
| Change from Month 0 to 2 | 20 | −2158.8 ± 146 | 20 | −2209.2 ± 113 | NS |
| Change from Month 0 to 3 | 20 | −3099.4 ± 200 | 20 | −2628.8 ± 498 | NS |
| Change from Month 0 to 4 | 20 | −4014.6 ± 271 | 20 | −3418.7 ± 564 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values >0.1)
*t-Test,
**paired t-test

TABLE 15

Weight Loss Study: Total Body Fat by DXA (g)

| | Formula CA | | Formula CB | | Formula CA |
| --- | --- | --- | --- | --- | --- |
| Parameter Measured | N | Mean ± SEM | N | Mean ± SEM | vs Formula CB* |
| Observed Month 0 | 20 | 7304.15 ± 414 | 20 | 7328.10 ± 417 | NS |
| Observed Month 1 | 20 | 6232.45 ± 396 | 20 | 6219.35 ± 459 | NS |
| Observed Month 2 | 20 | 5218.50 ± 357 | 20 | 5116.05 ± 411 | NS |
| Observed Month 3 | 20 | 4349.60 ± 302 | 20 | 4261.55 ± 384 | NS |
| Observed Month 4 | 20 | 3603.50 ± 300 | 20 | 3612.60 ± 323 | NS |
| Change from Month 0 to 1 | 20 | −1071.7 ± 88.6 | 20 | −1108.8 ± 98.4 | NS |
| Change from Month 0 to 2 | 20 | −2085.7 ± 164 | 20 | −2212.1 ± 11.6 | NS |
| Change from Month 0 to 3 | 20 | −2954.6 ± 179 | 20 | −3066.6 ± 136 | NS |
| Change from Month 0 to 4 | 20 | −3700.7 ± 249 | 20 | −3715.5 ± 184 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values >0.1)
*t-Test,
**paired t-test

TABLE 16

Weight Loss Study: Percent Body Fat by DXA (%)

| | Formula CA | | Formula CB | | Formula CA |
| --- | --- | --- | --- | --- | --- |
| Parameter Measured | N | Mean ± SEM | N | Mean ± SEM | vs Formula CB* |
| Observed Month 0 | 20 | 41.02 ± 1.01 | 20 | 41.17 ± 0.84 | NS |
| Observed Month 1 | 20 | 37.50 ± 1.3 | 20 | 37.01 ± 1.19 | NS |
| Observed Month 2 | 20 | 33.14 ± 1.52 | 20 | 32.38 ± 1.31 | NS |
| Observed Month 3 | 20 | 29.43 ± 1.34 | 20 | 28.39 ± 1.43 | NS |
| Observed Month 4 | 20 | 25.97 ± 1.47 | 20 | 25.52 ± 1.32 | NS |
| Change from Month 0 to 1 | 20 | −3.53 ± 0.53 | 20 | −4.17 ± 0.52 | NS |

TABLE 16-continued

Weight Loss Study: Percent Body Fat by DXA (%)

| Parameter Measured | Formula CA | | Formula CB | | Formula CA |
| --- | --- | --- | --- | --- | --- |
| | N | Mean ± SEM | N | Mean ± SEM | vs Formula CB* |
| Change from Month 0 to 2 | 20 | −7.89 ± 0.8 | 20 | −8.79 ± 0.66 | NS |
| Change from Month 0 to 3 | 20 | −11.59 ± 0.6 | 20 | −12.78 ± 0.8 | NS |
| Change from Month 0 to 4 | 20 | −15.05 ± 1.13 | 20 | −15.66 ± 0.8 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values >0.1)
*t-Test,
**paired t-test

TABLE 17

Weight Loss Study: Lean Mass by DXA (g)

| Parameter Measured | Formula CA | | Formula CB | | Formula CA |
| --- | --- | --- | --- | --- | --- |
| | N | Mean ± SEM | N | Mean ± SEM | vs Formula CB* |
| Observed Month 0 | 20 | 9816.85 ± 331 | 20 | 9794.05 ± 380 | NS |
| Observed Month 1 | 20 | 9627.50 ± 320 | 20 | 9762.55 ± 383 | NS |
| Observed Month 2 | 20 | 9762.95 ± 329 | 20 | 9820.35 ± 364 | NS |
| Observed Month 3 | 20 | 9696.60 ± 313 | 20 | 9830.45 ± 384 | NS |
| Observed Month 4 | 20 | 9533.05 ± 302 | 20 | 9696.20 ± 367 | NS |
| Change from Month 0 to 1 | 20 | −189.35 ± 77 | 20 | −31.50 ± 54.8 | NS |
| Change from Month 0 to 2 | 20 | −53.90 ± 92.8 | 20 | 26.30 ± 65 | NS |
| Change from Month 0 to 3 | 20 | −120.25 ± 86.8 | 20 | 36.40 ± 84.4 | NS |
| Change from Month 0 to 4 | 20 | −283.80 ± 132 | 20 | −97.85 ± 100 | NS |
| Month 0 vs 1** | | 0.02 | | NS | |
| Month 0 vs 2** | | NS | | NS | |
| Month 0 vs 3** | | NS | | NS | |
| Month 0 vs 4** | | 0.04 | | NS | |

NS = Not significant (i.e., p-values >0.1)
*t-Test,
**paired t-test

The results indicate that although the test animals lost lean muscle in the first one month of the study, the level of lean muscle was maintained during the study while the animals statistically lost about 20±5% body weight or about 50% of body fat to achieve about 30% of mean body fat.

The weight loss also resulted in a reduction of IGF-1 and leptin levels, which were maintained after weight loss. The results are shown below.

TABLE 18

Weight Loss Study: IGF-1(ng/ml)

| Parameter Measured | Formula CA | | Formula CB | | Formula CA |
| --- | --- | --- | --- | --- | --- |
| | N | Mean ± SEM | N | Mean ± SEM | vs Formula CB* |
| Observed Month 0 | 20 | 134.48 ± 7.6 | 20 | 132.05 ± 9.49 | NS |
| Observed Month 1 | 20 | 140.92 ± 11.7 | 20 | 131.25 ± 9.69 | NS |
| Observed Month 2 | 20 | 124.88 ± 9.34 | 20 | 126.07 ± 9.11 | NS |
| Observed Month 3 | 20 | 117.25 ± 8.79 | 20 | 119.73 ± 10.4 | NS |
| Observed Month 4 | 20 | 119.98 ± 9.76 | 20 | 111.48 ± 9.85 | NS |
| Change from Month 0 to 1 | 20 | 6.45 ± 7.36 | 20 | −0.79 ± 9.75 | NS |
| Change from Month 0 to 2 | 20 | −9.60 ± 6.49 | 20 | −5.97 ± 7.96 | NS |
| Change from Month 0 to 3 | 20 | −17.23 ± 6.87 | 20 | −12.32 ± 9.68 | NS |
| Change from Month 0 to 4 | 20 | −14.50 ± 7.2 | 20 | −20.56 ± 10.5 | NS |
| Month 0 vs 1** | | NS | | NS | |
| Month 0 vs 2** | | NS | | NS | |

TABLE 18-continued

Weight Loss Study: IGF-1(ng/ml)

| Parameter Measured | Formula CA | | Formula CB | | Formula CA vs Formula CB* |
|---|---|---|---|---|---|
| | N | Mean ± SEM | N | Mean ± SEM | |
| Month 0 vs 3** | | 0.02 | | NS | |
| Month 0 vs 4** | | 0.06 | | 0.06 | |

NS = Not significant (i.e., p-values >0.1)

*t-Test,

**paired t-test

TABLE 19

Weight Loss Study: Leptin (ng/ml)

| Parameter Measured | Formula CA | | Formula CB | | Formula CA vs Formula CB* |
|---|---|---|---|---|---|
| | N | Mean ± SEM | N | Mean ± SEM | |
| Observed Month 0 | 20 | 13.61 ± 1.8 | 20 | 13.95 ± 1.97 | NS |
| Observed Month 1 | 20 | 7.76 ± 0.92 | 20 | 7.46 ± 0.89 | NS |
| Observed Month 2 | 20 | 6.02 ± 0.83 | 20 | 5.67 ± 0.83 | NS |
| Observed Month 3 | 20 | 4.14 ± 0.48 | 20 | 6.24 ± 1.59 | NS |
| Observed Month 4 | 20 | 3.50 ± 0.98 | 20 | 4.86 ± 1.59 | NS |
| Change from Month 0 to 1 | 20 | −5.85 ± 1.21 | 20 | −6.49 ± 1.76 | NS |
| Change from Month 0 to 2 | 20 | −7.59 ± 1.18 | 20 | −8.27 ± 1.8 | NS |
| Change from Month 0 to 3 | 20 | −9.48 ± 1.56 | 20 | −7.71 ± 1.48 | NS |
| Change from Month 0 to 4 | 20 | −10.12 ± 1.44 | 20 | −9.08 ± 1.52 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | <0.01 | | <0.01 | |

NS = Not significant (i.e., p-values >0.1)

*t-Test,

**paired t-test

In addition, it was noted that the animals maintained their reduced weight for an additional four months and continued to lose weight.

Results are provided below.

TABLE 20

Weight Maintenance Study: Total Body Weight Maintained by DXA (g)

| Parameter Measured | Formula CA | | Formula CB | | Formula CA vs Formula CB* |
|---|---|---|---|---|---|
| | N | Mean ± SEM | N | Mean ± SEM | |
| Observed Month 0 | 20 | 13619.9 ± 520 | 20 | 14227.2 ± 604 | NS |
| Observed Month 1 | 20 | 13074.4 ± 487 | 20 | 13336.8 ± 617 | NS |
| Observed Month 2 | 20 | 13027.5 ± 495 | 20 | 13245.5 ± 600 | NS |
| Observed Month 3 | 20 | 13190.3 ± 465 | 20 | 13375.5 ± 615 | NS |
| Observed Month 4 | 20 | 13381.4 ± 495 | 20 | 13580.6 ± 586 | NS |
| Change from Month 0 to 1 | 20 | −545.50 ± 111 | 20 | −890.35 ± 418 | NS |
| Change from Month 0 to 2 | 20 | −592.40 ± 141 | 20 | −981.65 ± 429 | NS |
| Change from Month 0 to 3 | 20 | −429.60 ± 160 | 20 | −851.70 ± 444 | NS |
| Change from Month 0 to 4 | 20 | −238.50 ± 135 | 20 | −646.60 ± 416 | NS |
| Month 0 vs 1** | | <0.01 | | 0.05 | |
| Month 0 vs 2** | | <0.01 | | 0.03 | |
| Month 0 vs 3** | | 0.01 | | 0.07 | |
| Month 0 vs 4** | | 0.09 | | NS | |

NS = Not significant (i.e., p-values >0.1)

*t-Test,

**paired t-test

TABLE 21

Weight Maintenance Study: Total Body Fat by DXA (g)

| Parameter Measured | Formula CA | | Formula CB | | Formula CA vs |
|---|---|---|---|---|---|
| | N | Mean ± SEM | N | Mean ± SEM | Formula CB* |
| Observed Month 0 | 20 | 3603.50 ± 300 | 20 | 3612.60 ± 323 | NS |
| Observed Month 1 | 20 | 3056.20 ± 258 | 20 | 3216.20 ± 324 | NS |
| Observed Month 2 | 20 | 2502.00 ± 233 | 20 | 2699.15 ± 304 | NS |
| Observed Month 3 | 20 | 2956.20 ± 257 | 20 | 3019.50 ± 349 | NS |
| Observed Month 4 | 20 | 3129.45 ± 260 | 20 | 3216.25 ± 316 | NS |
| Change from Month 0 to 1 | 20 | −547.30 ± 178 | 20 | −396.40 ± 87 | NS |
| Change from Month 0 to 2 | 20 | −1101.5 ± 187 | 20 | −913.45 ± 143 | NS |
| Change from Month 0 to 3 | 20 | −647.30 ± 213 | 20 | −593.10 ± 123 | NS |
| Change from Month 0 to 4 | 20 | −474.05 ± 199 | 20 | −396.35 ± 158 | NS |
| Month 0 vs 1** | | <0.01 | | <0.01 | |
| Month 0 vs 2** | | <0.01 | | <0.01 | |
| Month 0 vs 3** | | <0.01 | | <0.01 | |
| Month 0 vs 4** | | 0.03 | | 0.02 | |

NS = Not significant (i.e., p-values >0.1)
*t-Test,
**paired t-test

TABLE 22

Weight Maintenance Study: Percent Body Fat by DXA (%)

| Parameter Measured | Formula CA | | Formula CB | | Formula CA |
|---|---|---|---|---|---|
| | N | Mean ± SEM | N | Mean ± SEM | vs Formula CB* |
| Observed Month 0 | 20 | 25.97 ± 1.47 | 20 | 25.52 ± 1.32 | NS |
| Observed Month 1 | 20 | 23.03 ± 1.51 | 20 | 23.42 ± 1.48 | NS |
| Observed Month 2 | 20 | 18.90 ± 1.46 | 20 | 19.81 ± 1.48 | NS |
| Observed Month 3 | 20 | 22.13 ± 1.61 | 20 | 21.73 ± 1.75 | NS |
| Observed Month 4 | 20 | 23.04 ± 1.58 | 20 | 23.15 ± 1.5 | NS |
| Change from Month 0 to 1 | 20 | −2.94 ± 1.09 | 20 | −2.10 ± 0.59 | NS |
| Change from Month 0 to 2 | 20 | −7.07 ± 1.09 | 20 | −5.71 ± 0.83 | NS |
| Change from Month 0 to 3 | 20 | −3.85 ± 1.28 | 20 | −3.79 ± 0.83 | NS |
| Change from Month 0 to 4 | 20 | −2.94 ± 1.26 | 20 | −2.37 ± 0.94 | NS |
| Month 0 vs 1** | | 0.01 | | <0.01 | |
| Month 0 vs 2** | | <0.01 | | <0.01 | |
| Month 0 vs 3** | | <0.01 | | <0.01 | |
| Month 0 vs 4** | | 0.03 | | 0.02 | |

NS = Not significant (i.e., p-values >0.1)
*t-Test,
**paired t-test

TABLE 23

Weight Maintenance Study: Lean Mass by DXA (g)

| Parameter Measured | Formula CA | | Formula CB | | Formula CA |
|---|---|---|---|---|---|
| | N | Mean ± SEM | N | Mean ± SEM | vs Formula CB* |
| Observed Month 0 | 20 | 9533.05 ± 302 | 20 | 9696.20 ± 367 | NS |
| Observed Month 1 | 20 | 9542.55 ± 338 | 20 | 9637.65 ± 381 | NS |
| Observed Month 2 | 20 | 10052.8 ± 370 | 20 | 10067.1 ± 401 | NS |
| Observed Month 3 | 20 | 9764.00 ± 345 | 20 | 9875.10 ± 386 | NS |
| Observed Month 4 | 20 | 9781.45 ± 352 | 20 | 9887.05 ± 382 | NS |
| Change from Month 0 to 1 | 20 | 9.50 ± 102 | 20 | −58.55 ± 69.2 | NS |
| Change from Month 0 to 2 | 20 | 519.70 ± 122 | 20 | 370.85 ± 80 | NS |
| Change from Month 0 to 3 | 20 | 230.95 ± 111 | 20 | 178.90 ± 59.2 | NS |
| Change from Month 0 to 4 | 20 | 248.40 ± 112 | 20 | 190.85 ± 79.3 | NS |
| Month 0 vs 1** | | NS | | NS | |
| Month 0 vs 2** | | <0.01 | | <0.01 | |
| Month 0 vs 3** | | 0.05 | | <0.01 | |
| Month 0 vs 4** | | 0.04 | | 0.03 | |

NS = Not significant (i.e., p-values >0.1)
*t-Test,
**paired t-test

TABLE 24

Weight Maintenance Study: Food Intake

| Parameter Measured | Formula CA | | Formula CB | |
| --- | --- | --- | --- | --- |
| | N | Mean | N | Mean |
| Observed Month 1 | 20 | 216 | 20 | 220 |
| Observed Month 2 | 20 | 281 | 20 | 279 |
| Observed Month 3 | 20 | 337 | 20 | 335 |
| Observed Month 4 | 20 | 360 | 20 | 354 |
| Change from Month 1 to 2 | 20 | 65 | 20 | 58 |
| Change from Month 1 to 3 | 20 | 121 | 20 | 114 |
| Change from Month 1 to 4 | 20 | 144 | 20 | 133 |

Results of the weight maintenance study showed that in the four months of weight maintenance, dogs maintained their weight while increasing their food intake by 66% (359 grams vs 21.6 grams) consuming Formula CA, or 61% (354 grams vs 220 grams) consuming Formula CB. The dogs consuming either Formula CA or CB also continued to lose body fat (P<0.03) while maintaining their body weight. In addition, dogs fed with Formula CA or CB had increased lean muscle mass while maintaining their body weight.

In view of the foregoing, the following embodiments of the invention are provided without limitation.

One embodiment of the invention provides a pet food composition that includes myristic acid, such as myristic acid from a plant source, and beta-carotene, such as beta-carotene from a plant source, in amounts effective to prevent or treat obesity in a companion animal, such as a canine or feline. The myristic acid source may, for example, include or consist of coconut oil, palm oil, palm kernel oil, crystalline myristate, or mixtures thereof. The beta-carotene source may, for example, include or consist of at least one of tomato pomace, carrot powder, kale, pumpkin, spearmint, spinach, squash, sweet potato, or mixtures thereof. The amount of beta-carotene in the composition may, for example, be at least 2 parts per million (ppm), such as in the range 2-4 ppm. The pet food compositions may optionally include lipoic acid.

In one embodiment, the myristic acid is in an amount of at least about 0.1%, at least about 0.2%, and at least about 0.3%.

In one embodiment, myristic acid is at least predominantly provided by coconut oil in the composition, and beta-carotene is at least substantially provided by tomato pomace, carrot powder or mixtures thereof in the composition. In another embodiment of the invention, the amount of tomato pomace is about 2 wt % to about 8 wt %, the amount of coconut oil is about 0.5 wt % to about 6.0%, and the amount of carrot powder is about 0.1 wt % to about 2.0 wt %.

In a further embodiment, the composition includes from about 20 wt % to about 50 wt % of total protein, from about 15 wt % to about 50 wt % of total dietary fiber, and from about 3 wt % to about 15 wt % of fat.

A related embodiment of the invention provides a method for preventing or treating obesity in a companion animal, such as a canine or a feline, which includes feeding to a companion animal in need of prevention or treatment of obesity a composition of the invention. The composition may, for example, be fed to the animal as its primary or sole nutritionally complete food on a daily basis. The feeding prevents or treats obesity without or substantial concomitant lose of lean muscle mass.

The composition may be fed to the animal at least once daily, for example, until the animal reaches its normal weight range. The at least once daily feeding of the composition to the animal may be continued after the animal reaches its normal weight range, so that the animal maintains its normal weight range. The composition may, for example, be fed at least once daily to the animal for at least one week, for at least one month, for at least 2 months, or for at least 3 months. As demonstrated herein, such feeding reduces the serum level of leptin and insulin-like growth factor-1 (IGF-1) in the animal.

A further embodiment provides the use of myristic acid, such as a myristic acid plant source, for example, coconut oil, and a beta-carotene source, such as a beta-carotene plant source, for example at least one of tomato pomace and carrot powder, for the manufacture of a weight-loss and maintenance pet food composition for a companion animal, such as a canine or a feline.

Natural plant sources of myristic acid and beta-carotene are preferred but the invention is not limited to such sources. Corresponding embodiments to those described, but using purified or synthetic myristic acid and/or beta-carotene, are also within the scope of the invention.

What is claimed is:

1. A nutritionally balanced pet food composition comprising a myristic acid source and a beta-carotene source, in amounts effective to prevent or treat obesity in a companion animal in need thereof, wherein myristic acid is present in the composition in an amount of at least 0.3%, and wherein beta-carotene is present in the composition in an amount of from 2 ppm to 4 ppm,
wherein the pet food composition further comprises 20 to 50 wt % of protein, which comprises from 1 to 4 wt % of arginine; from 0.01 to 1.5 wt % of cystine; from 0.01 to 1.5 wt % of histidine; from 0.1 to 3 wt % of isoleucine; from 2 to 6 wt % of leucine; from 0.1 to 4 wt % lysine, from 0.1 to 3 wt % of methionine; from 0.1 to 4 wt % of phenylalanine; from 0.1 to 3 wt % threonine; from 0.01 to 2 wt % tryptophan; from 0.1 to 4 wt % of tyrosine; and from 0.5 to 4 wt % of valine.

2. The composition of claim 1 wherein said myristic acid source comprises coconut oil, and said beta-carotene source comprises at least one of tomato pomace and carrot powder.

3. The composition of claim 2 wherein the amount of tomato pomace is about 2 wt % to about 8 wt %; the amount of coconut oil is about 0.5 wt % to about 6.0%; and
the amount of carrot powder is about 0.1 wt % to about 2.0 wt %.

4. The composition of claim 1 comprising:
from about 15 wt % to about 50 wt % of total dietary fiber; and
from about 3 wt % to about 15 wt % of fat.

5. The composition of claim 1, further comprising lipoic acid.

6. The composition of claim 1, wherein the companion animal is a canine or feline.

7. A method for preventing or treating obesity in a companion animal comprising feeding to a companion animal in need of prevention or treatment of obesity, a composition of claim 1.

8. The method of claim 7, wherein said feeding prevents or treats obesity without concomitant loss of lean muscle mass.

9. The method of claim 7, wherein the composition is fed to the animal at least once daily.

10. The method of claim 7, wherein the composition is fed at least once daily to the animal until the animal reaches its normal weight range.

11. The method of claim 10, wherein the at least once daily feeding of the composition to the animal is continued after the animal reaches its normal weight range, whereby the animal maintains its normal weight range.

12. The method of claim 7, wherein the composition is fed at least once daily to the animal for at least one week.

13. The method of claim 7, wherein the composition is fed at least once daily to the animal for at least one month.

14. The method of claim 7, wherein the composition is fed at least once daily to the animal for at least two months.

15. The method of claim 7, wherein the treatment or prevention of obesity comprises reducing the serum level of leptin and insulin-like growth factor-1 (IGF-1) in the animal.

16. The method of claim 7, wherein the companion animal is a canine or feline.

\* \* \* \* \*